US00PP34943P2

(12) United States Plant Patent
Nishikawa

(10) Patent No.: US PP34,943 P2
(45) Date of Patent: Jan. 24, 2023

(54) ***DELOSPERMA* PLANT NAMED 'T1821'**

(50) Latin Name: *Delosperma nubigenum*
Varietal Denomination: T1821

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 17/699,453

(22) Filed: Mar. 21, 2022

(30) Foreign Application Priority Data

Sep. 8, 2021 (QZ) ..... PBR20212227

(51) Int. Cl.
*A01H 6/00* (2018.01)
*A01H 5/02* (2018.01)

(52) U.S. Cl.
USPC ..... Plt./422

(58) Field of Classification Search
USPC ..... Plt./422
See application file for complete search history.

*Primary Examiner* — Annette H Para
(74) *Attorney, Agent, or Firm* — Penny J. Aguirre

(57) ABSTRACT

A new cultivar of *Delosperma* plant named 'T1821' that is characterized by its very large flowers, its very floriferous and long blooming flowering habit; blooming from early summer to early autumn, its flowers that are intense orange in color, and its low-growing plant habit.

2 Drawing Sheets

Botanical classification: *Delosperma nubigenum.*
Variety denomination: 'T1821'.

CROSS-REFERENCE TO A RELATED APPLICATIONS

This application claims priority to European Community Plant Variety Office (CPVO) Plant Breeder's Rights Application No. 2021/2227 filed on Sep. 8, 2021, under 35 U.S.C. 119(f), the entire contents of which is incorporated by reference herein. This application is also co-pending with a U.S. Plant Patent Applications for a plant derived from the same breeding program entitled *Delosperma* Plant Named 'WOWDOY2' (U.S. Plant Pat. No. 25,645) and *Delosperma* Plant Named 'WOWDOY3' (U.S. Plant Pat. No. 25,600).

BACKGROUND OF THE INVENTION

The present invention relates to a new and distinct cultivar of *Delosperma* plant, botanically known as *Delosperma nubigenum* 'T1821' and will be referred to hereinafter by its cultivar name, 'T1821'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with floriferous blooming habits and large flowers in a unique range of flower colors.

'T1821' was selected in the Inventor's trial garden in May of 2018 as a single unique plant from amongst the seedlings derived from crosses between unnamed and unpatented plants from the Inventor's breeding program. Seeds were pooled from the crosses and therefore the exact parentage is unknown.

Asexual propagation of the new cultivar was first accomplished by stem cuttings in September of 2018 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'T1821' as a unique cultivar of *Delosperma.*

1. 'T1821' exhibits very large flowers.
2. 'T1821' exhibits a very floriferous and long blooming flowering habit; blooming from early summer to early autumn.
3. 'T1821' exhibits flowers that are intense orange in color.
4. 'T1821' exhibits a low-growing plant habit.

'T1821' can be most closely compared to the *Delosperma* cultivars 'WOWDOY3' and 'WOWDOY2'. 'WOWDOY3' is similar to 'T1821' in having a low growing plant habit and flowers with orange coloration. 'WOWDOY3' differs from 'T1821' in having lighter colored orange flowers with larger yellow centers, a less floriferous blooming habit, and smaller flowers. 'WOWDOY2' is similar to 'T1821' in having a low-growing plant habit. 'WOWDOY2' differs from 'T1821' in having flowers that are much smaller in size and red- orange in color with a larger yellow center and in being less floriferous.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by darwinperennials, ballseed, ecgrowers, agriexpo.online, jamesgreenhouses, cornellfarms, garden, misstate, visionspictures, centertonnursery, gpnmag, theivyfarm, gulleygreenhouse, online flippingbook, perennialmarket, costafarmsevents, irp- cdn. multiscreensite, ppandl, lineaverdemagazine, globeplanter, glpksp, onliant.and griffins.

BRIEF DESCRIPTION OF THE DRAWINGS

The accompanying color photographs illustrate the overall appearance and distinct characteristics of the new *Delosperma*.

The photograph in FIG. 1 was taken of a 6-month-old plant as grown in a 3-liter container outdoors in Chicago, Ill. and provides a top view of 'T1821' in bloom.

Figure 1:
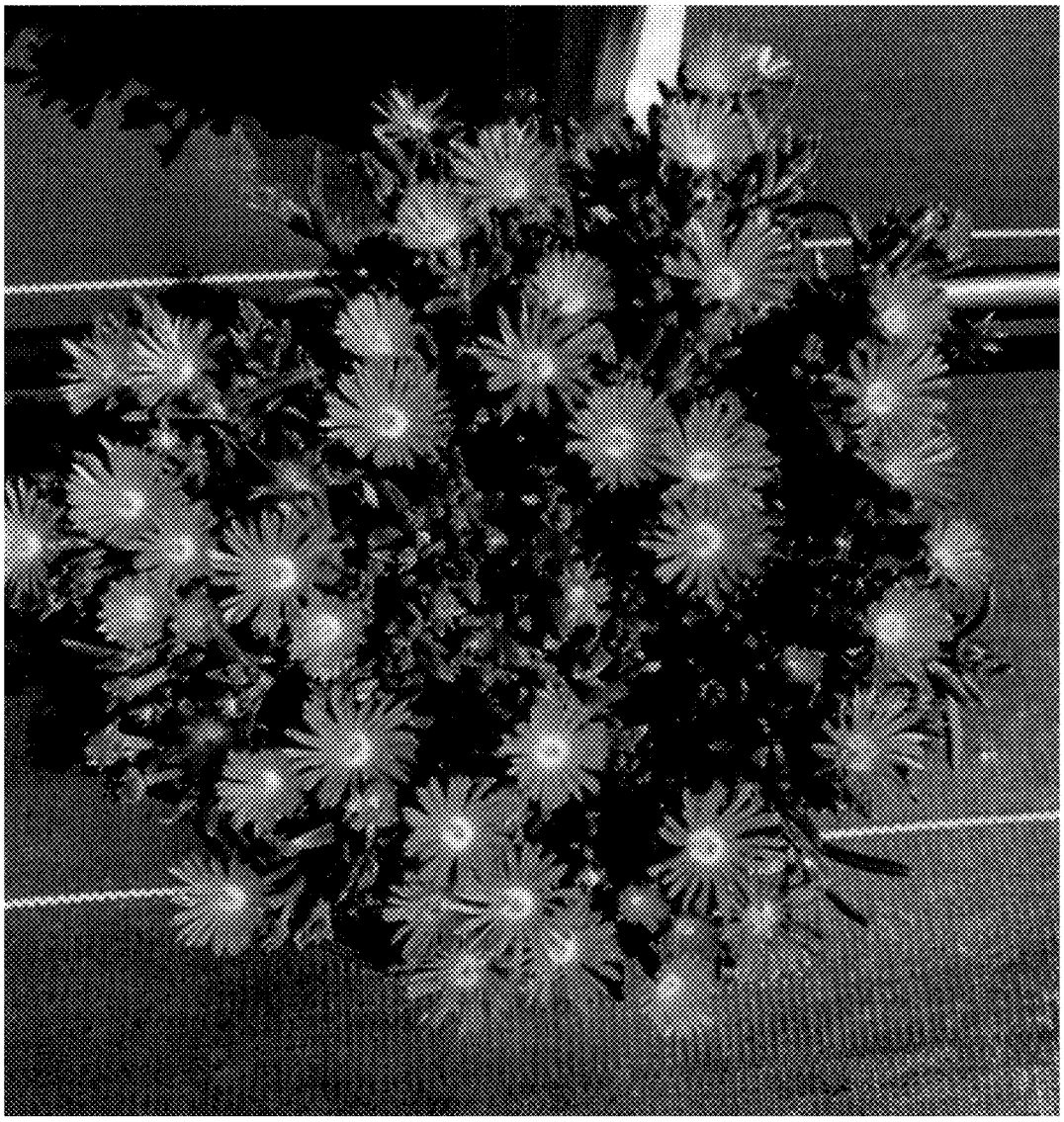
Figure 2:
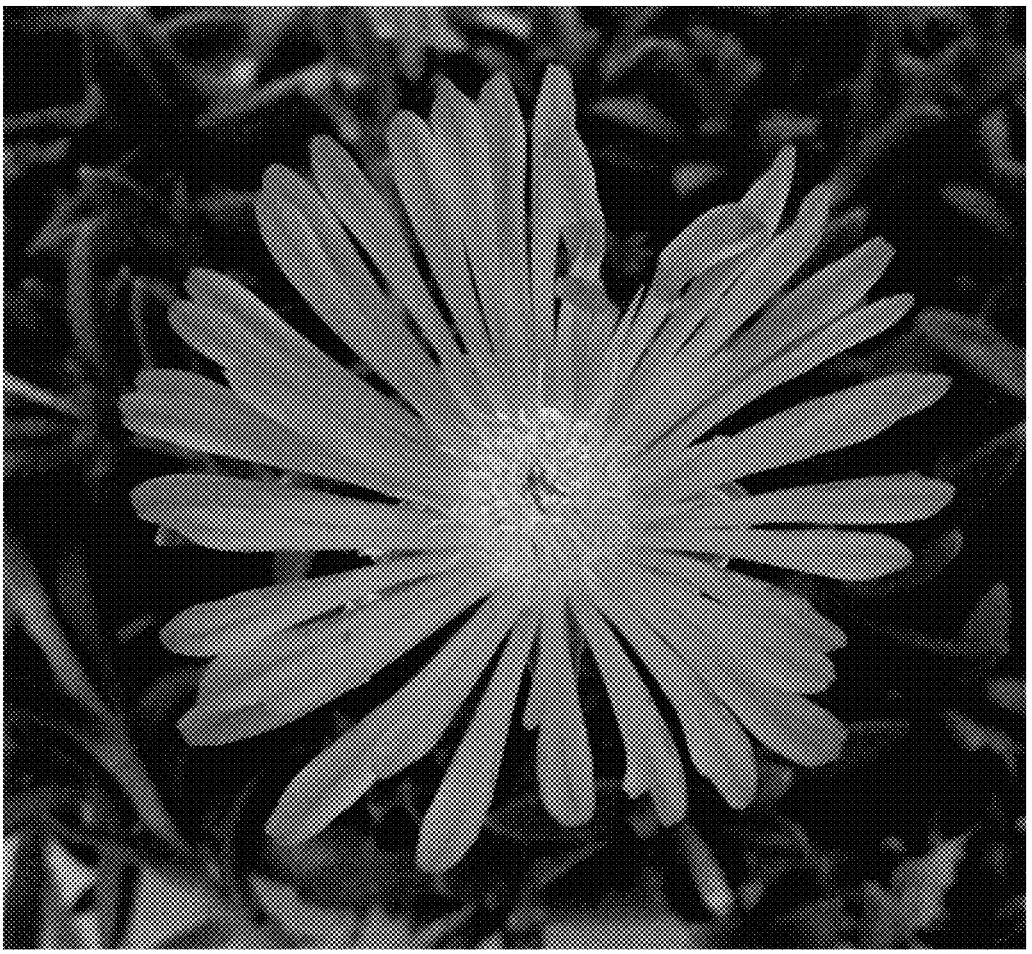

The photograph in FIG. 2 was taken of a plant 4 months in age as grown in an unheated greenhouse in a 15-cm container in Noordwijkerhout, The Netherlands and provides a close-up view of a flower of 'T1821'.

The colors in the photograph may differ slightly from the color values cited in the detailed botanical description, which accurately describe the colors of the new *Delosperma*.

DETAILED BOTANICAL DESCRIPTION

The following is a detailed description of 4-month-old plants of the new cultivar as grown in 15-cm containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with the 2015; reprint 2019 Colour Chart of The Royal Horticultural Society, London, England, except where general color terms of ordinary dictionary significance are used.

General description:

*Blooming period*.—Blooms from early summer to early autumn in The Netherlands.

*Plant type*.—Evergreen perennial.

*Plant habit*.—Flattened, prostrate.

*Height and spread*.—Reaches an average of 7 cm in height and about 25 cm in width as a 4-month old plant in a container.

*Cold hardiness*.—Observed to be hardy to at least U.S.D.A. Zone 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a plug to young plant in a P9 container.

*Growth habit*.—Moderate.

Stem description:

*Shape*.—Round.

*Stem color*.—Young stems; 145B with 183A, older stems 145A and 199C.

*Stem size*.—Lateral branches; an average of 11.5 cm in length and 3 mm in diameter.

*Internode length*.—An average of 1.7 cm.

*Stem substance*.—Succulent.

*Stem surface*.—Moderately glossy, moderately pubescent with very short glandular hairs; an average of 0.2 mm in length and closest to 155C in color.

*Branching habit*.—Freely branching both basal and lateral, an average of 12 lateral branches per stem.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, sparsely to moderately pubescent with very short glandular hairs; an average of 0.2 mm in length, 157D in color.

*Leaf color*.—137A, base 145A.

*Leaf size*.—About 2.7 cm in length and 5 mm in width.

*Leaf quantity*.—Average of 12 (6 pairs) per lateral branch.

*Leaf attachment*.—Sessile.

Inflorescence description:

*Inflorescence type*.—Flowers solitary, terminal.

*Flower number*.—An average of 1 per lateral stem.

*Flower fragrance*.—Faint, sweet and pleasant.

*Flower aspect*.—Outward to upright.

*Flower longevity*.—A few days, self-cleaning.

*Flower type*.—Single.

*Flower size*.—Average of 5 cm in diameter and 1.3 cm in depth.

*Flower buds*.—Broadly ovate to oblong in shape, an average of 1 cm in length and 5 mm in diameter, color; 138A with sepal portion 137C, surface texture is smooth and glassy with the sepal portion smooth and dull.

*Calyx*.—Rotate in shape, average of 6 mm in depth and 1.8 cm in diameter.

*Sepals*.—5, rotate, ovate in shape, margin entire, an average of 7 mm in length and 3 mm in width, broadly acute apex, broadly cuneate base, surface is smooth and dull, color young upper and lower surface; 137C, base 145A, color mature upper and lower surface; 137A.

*Petals*.—An average of 42 per flower, rotate and slightly curved downward, oblanceolate in shape, surface is smooth and glossy on both surfaces, margin entire, apex obtuse, base cuneate, an average of 2.1 cm in length and 2.3 mm in width, color: opening and fully open upper and lower surface 22A, base 28A, non-fading on both surfaces.

*Petaloids*.—An average of 20 per flower, rotate and near vertical surrounding stamens, lanceolate in shape, moderately to highly glossy on both surfaces, margin entire, apex obtuse, base truncate, an average of 1 cm in length and 1 mm in width, color: upper and lower surface 22A, with a hint of 28A.

*Peduncle*.—Average of 1.8 cm in length and 2 mm in diameter, straight on top of lateral branch at 0°, color; a blend between 145A, surface moderately glossy, sparsely to moderately pubescent with very short glandular hairs.

*Pedicel*.—None.

Reproductive organs:

*Pistils*.—5, an average of 2 mm in length, stigma; triangular shaped, style and stigma; (not distinguishable) combined an average of 2 mm in length and 151B in color, ovary; 143C in color.

*Stamens*.—Average of 60, 12A in color, anthers; dorsifixed and narrowly oblong in shape, an average of 0.5 mm in diameter, filaments; 4 mm in length, NN155D in color, anthers; NN155D in color, pollen; moderate to high in quantity and 6A in color.

*Fruit*.—Fruit and seed production was not observed under the conditions tested.

It is claimed:

1. A new and distinct variety of *Delosperma* plant named 'T1821' as described and illustrated herein.

* * * * *